United States Patent [19]

Orban et al.

[11] 3,943,139

[45] Mar. 9, 1976

[54] PROCESS FOR THE MANUFACTURE OF TRIACETONE-AMINE

[75] Inventors: Ivan Orban; Jean Rody, both of Basel, Switzerland

[73] Assignee: CIBA-GEIGY Corporation, Ardsley, N.Y.

[22] Filed: Oct. 4, 1973

[21] Appl. No.: 403,360

[30] Foreign Application Priority Data

Oct. 20, 1972 Switzerland........................ 15425/72
July 5, 1973 Switzerland......................... 9849/73

[52] U.S. Cl. .......................................... 260/293.89
[51] Int. Cl.² ...................................... C07D 211/02
[58] Field of Search ............................... 260/293.89

[56] References Cited

UNITED STATES PATENTS 3,513,170  5/1970  Murayama et al............... 260/294.7

OTHER PUBLICATIONS

Rodd, "Chemistry of Carbon Compounds," Vol. IA, Elsevier, New York, (1951), pp. 533–535.

*Primary Examiner*—G. Thomas Todd
*Attorney, Agent, or Firm*—Nestor W. Shust

[57] ABSTRACT

A new process for producing triacetone-amine by reacting phoron and ammonia under pressure and higher temperature.

12 Claims, No Drawings

PROCESS FOR THE MANUFACTURE OF TRIACETONE-AMINE

The invention relates to a new process for the manufacture of triacetone-amine.

Various processes have been proposed for the manufacture of triacetone-amine. [E. G. Rozantsev, Pharm. Chem. J. 5. 42–46 (1971)]. All these methods suffer from the disadvantage of a long reaction time coupled with relatively low yield. Furthermore, the by-products to be found in the aqueous liquors present serious ecological problems in the case of all these processes.

For example, in the known process for the manufacture of triacetone-amine starting from phorone and ammonia solution, a yield of 68% is obtained for a reaction time of 1 to 2 days. At the same time a relatively large amount of aqueous ammonia solution is required. To isolate the triacetone-amine, it must be salted out and filtered off. In spite of salting out, the aqueous mother liquor always retains 1 to 2% of the very readily water-soluble triacetone-amine, which means an additional contamination of the effluent.

A new more economical process for the manufacture of triacetone-amine by reaction of phorone with an aqueous solution of ammonia has now been discovered, which is characterised in that the reaction is carried out at elevated temperature in an aqueous solution which is under gaseous ammonia at elevated pressure. This shortens the reaction time and increases the yield and it is furthermore possible to work with a substantially lower amount of water than in the case of the previously known processes. The reduced amount of water makes it possible to fill the reaction product directly into a container where it solidifies to a mass of crystals after cooling. As a result, the filtration required in the previously known processes, and the effluent problems associated therewith, are eliminated.

An even better yield is obtained according to the new process if the reaction is carried out in the presence of alkali metal hydroxide or alkaline earth metal hydroxide. For example, 1 to 6 mol%, preferably 3 mol%, calculated relative to the phorone, can be added. Examples of alkali metal hydroxides which can be used are lithium hydroxide, sodium hydroxide or potassium hydroxide, and examples of alkaline earth metal hydroxides which can be used are magnesium hydroxide, calcium hydroxide, strontium hydroxide or barium hydroxide.

It is critical for the new process that the reaction is carried out at elevated temperature in a solution which is in contact with gaseous ammonia under excess pressure and that this excess pressure of the ammonia atmosphere is maintained during the reaction. The excess pressure should preferably be at least 0.2 bar and particularly preferentially 1 to 5 and 1 to 3 bars. The elevated temperature is preferably 60° to 110°C and particularly preferentially 90° to 100°C.

In a preferred embodiment of the new process, a small amount of water is used. In the preferred embodiment, the ratio of water to phorone should be at least 1:1 and should preferably be between 2:1 and 4:1. The triacetone-amine obtained is an intermediate product for the manufacture of light protection agents such as, for example, the light protection agents of French Patent No. 2,089,773 or of Belgian Patent No. 778,451. The invention is described in more detail in the examples which follow. In these, per cent (%) denote per cent by weight.

EXAMPLE 1

72 ml of 24% strength ammonia solution and 100 g of phorone are initially introduced into a 300 ml stainless steel autoclave at room temperature. The autoclave is sealed and brought, three times in succession, to 2 bars excess pressure with ammonia gas for a short period, whilst stirring, the pressure in each case again being released. Thereafter the temperature is raised over the course of 1 hour to 95°C, starting at 1 bar excess pressure, whilst stirring well. During heating up, the ammonia pressure is allowed to rise to only 2 bars excess pressure by blowing off gas. Thereafter the reaction mixture is kept for approx. 4 hours at 95°C and 2 bars excess pressure. During the first 2 hours the mixture takes up ammonia whilst during the next 2 hours ammonia is evolved. The contents of the autoclave are cooled to 60°C and the liquid reaction mixture is run out. On cooling, it solidifies to a pale yellowish crystal mass of triacetone-amine hydrate. 160 g of crude product having a triacetone-amine content of 65% are obtained, corresponding to a theoretical yield of 93%.

EXAMPLE 2

30 g of water and 100 g of phorone are initially introduced at room temperature into a 300 ml stainless steel autoclave. The autoclave is sealed and is brought three times in succession to 2 bars excess pressure with ammonia gas for a short time, whilst stirring, the pressure being released in each case. Thereafter, the temperature is raised to 95°C over the course of 1 hour, whilst stirring well. During heating up, the ammonia pressure is allowed to rise to only 1.3 bars excess pressure, by blowing off gas. Thereafter the reaction mixture is kept for approx. 5 hours at 95°C and 1.3 bars excess pressure. During the first 2.5 hours the mixture takes up ammonia and during the next 2.5 hours ammonia is evolved. The contents of the autoclave are cooled to 60°C and the liquid reaction mixture is run out. On cooling, it solidifies to a pale yellowish crystal mass of 142 g of triacetone-amine hydrate with a triacetone-amine content of 72.5%, which corresponds to a theoretical yield of 92%.

EXAMPLE 3

72 ml of 24% strength ammonia solution, 100 g of phorone and 0.05 g of lithium hydroxide (= 0.002 mol), dissolved in 4 ml of water, are initially introduced at room temperature into a 300 ml stainless steel autoclave. The autoclave is sealed and brought three times in succession to 2 bars excess pressure with ammonia gas for a short time, whilst stirring, the pressure being released in each case. Thereafter, the temperature is raised to 95°C over the course of 1 hour, starting at 1 bar excess pressure, whilst stirring well. During heating up, the ammonia pressure is allowed to rise to only 2 bars excess pressure, by blowing off gas. Thereafter the reaction mixture is kept at 95°C and 2 bars excess pressure for approx. 4 hours. During the first 2 hours the mixture takes up ammonia and during the next 2 hours ammonia is evolved. The autoclave contents are cooled to 60°C and the liquid reaction mixture is run out. On cooling, it solidifies to a pale yellowish crystal mass of triacetone-amine hydrate. 169 g of crude product having a triacetone-amine content of 65% are obtained, corresponding to a theoretical yield of 98%.

On replacing the 0.002 mol of lithium hydroxide used in this example by equimolar amounts of other alkali metal hydroxides or alkaline earth metal hydroxides, the following yields are obtained:

| Alkali metal hydroxide or alkaline earth metal hydroxide | Amount | Yield of triacetone-amine, % of theory |
|---|---|---|
| NaOH | 0.002 mol | 96% |
| Ca(OH)$_2$ | 0.002 mol | 94% |
| Ba(OH)$_2$ | 0.002 mol | 93% |

What we claim is:

1. Process for the manufacture of triacetone-amine by reaction of phorone with an equeous solution of ammonia, characterised in that the reaction is carried out under gaseous ammonia at not less than 0.2 bar excess pressure at 60° to 110°C and using a molar ratio of water to phorone of at least 1:1.

2. Process according to claim 1, characterised in that the reaction is carried out under gaseous ammonia at 1 to 5 bars excess pressure.

3. Process according to claim 1, characterised in that the reaction is carried out under gaseous ammonia at 1 to 3 bars excess pressure.

4. Process according to claim 1, characterised in that the reaction is carried out at 90° to 100°C.

5. Process according to claim 1, characterised in that the molar ratio of water to phorone is 2:1 to 4:1.

6. Process according to claim 1, characterised in that the reaction is carried out in the presence of alkali metal hydroxide or alkaline earth metal hydroxide.

7. Process according to claim 6, characterised in that the reaction is carried out in the presence of 1 to 6 mol% of alkali metal hydroxide or alkaline earth metal hydroxide calculated relative to the phorone.

8. Process according to claim 7, characterised in that the reaction is carried out in the presence of 3 mol% of alkali metal hydroxide or alkaline earth metal hydroxide calculated relative to the phorone.

9. Process according to claim 6, characterised in that lithium hydroxide is used as the alkali metal hydroxide.

10. Process according to claim 6, characterised in that sodium hydroxide is used as the alkali metal hydroxide.

11. Process according to claim 6, characterised in that calcium hydroxide is used as the alkaline earth metal hydroxide.

12. Process according to claim 6, characterised in that barium hydroxide is used as the alkaline earth metal hydroxide.

* * * * *